ated on Jul. 21, 1999

(12) United States Patent
Modlin et al.

(10) Patent No.: US 6,486,947 B2
(45) Date of Patent: Nov. 26, 2002

(54) DEVICES AND METHODS FOR SAMPLE ANALYSIS

(75) Inventors: Douglas N. Modlin, Palo Alto, CA (US); Amer El-Hage, Menlo Park, CA (US); John C. Owicki, Palo Alto, CA (US)

(73) Assignee: LJL BioSystems, Inc., Sunnyvale, CA (US)

( * ) Notice: Subject to any disclaimer, the term of this patent is extended or adjusted under 35 U.S.C. 154(b) by 0 days.

(21) Appl. No.: 09/767,434

(22) Filed: Jan. 22, 2001

(65) Prior Publication Data

US 2001/0006417 A1 Jul. 5, 2001

Related U.S. Application Data

(63) Continuation of application No. PCT/US99/16453, filed on Jul. 21, 1999
(60) Provisional application No. 60/093,768, filed on Jul. 22, 1998, provisional application No. 60/143,185, filed on Jul. 9, 1999, provisional application No. 60/094,275, filed on Jul. 27, 1998, provisional application No. 60/094,276, filed on Jul. 27, 1998, provisional application No. 60/094,306, filed on Jul. 27, 1998, provisional application No. 60/100,817, filed on Sep. 18, 1998, provisional application No. 60/100,951, filed on Sep. 18, 1998, provisional application No. 60/104,964, filed on Oct. 20, 1998, provisional application No. 60/114,209, filed on Dec. 29, 1998, provisional application No. 60/116,113, filed on Jan. 15, 1999, provisional application No. 60/117,278, filed on Jan. 26, 1999, provisional application No. 60/119,884, filed on Feb. 12, 1999, provisional application No. 60/121,229, filed on Feb. 23, 1999, provisional application No. 60/124,686, filed on Mar. 16, 1999, provisional application No. 60/125,346, filed on Mar. 19, 1999, provisional application No. 60/126,661, filed on Mar. 29, 1999, provisional application No. 60/130,149, filed on Apr. 20, 1999, provisional application No. 60/132,262, filed on May 3, 1999, provisional application No. 60/132,263, filed on May 3, 1999, provisional application No. 60/136,566, filed on May 28, 1999, provisional application No. 60/138,311, filed on Jun. 9, 1999, provisional application No. 60/138,438, filed on Jun. 10, 1999, provisional application No. 60/138,737, filed on Jun. 11, 1999, provisional application No. 60/138,893, filed on Jun. 11, 1999, provisional application No. 60/142,721, filed on Jul. 7, 1999, and provisional application No. 60/135,284, filed on May 21, 1999.

(51) Int. Cl.[7] .................................................. G01N 7/10
(52) U.S. Cl. ..................... 356/246; 356/244; 356/36; 422/82.05; 422/102; 422/104
(58) Field of Search ........................ 356/36, 244, 246, 356/440, 436; 250/576, 459.1, 491.1; 422/52, 63, 65, 82.05, 82.68, 102, 104

(56) References Cited

U.S. PATENT DOCUMENTS

| 2,056,791 A | * | 10/1936 | Logan ......................... 356/244 |
| 4,053,381 A | * | 10/1977 | Hamblen et al. ........... 356/244 |

(List continued on next page.)

FOREIGN PATENT DOCUMENTS

| JP | 05209832 | * | 8/1993 |
| JP | 08086754 | * | 4/1996 |
| WO | WO 00/04364 | * | 1/2000 |

\* cited by examiner

Primary Examiner—Frank G. Font
Assistant Examiner—Sang H. Nguyen
(74) Attorney, Agent, or Firm—Kolisch Hartwell, P.C.

(57) ABSTRACT

Devices and methods for containing and analyzing small sample volumes that are sandwiched between solid surfaces. The devices may include an automated drive mechanism that controls the relative positions of the surfaces and an environmental-control mechanism that controls the humidity, temperature, and/or other environmental conditions around the small sample volume. In some embodiments, at least one of the surfaces has a light-transmissive window for allowing optical analysis of a sample contained between the surfaces.

18 Claims, 5 Drawing Sheets

U.S. PATENT DOCUMENTS

| | | | | |
|---|---|---|---|---|
| 4,599,315 A | * | 7/1986 | Terasaki et al. | 356/246 |
| 4,746,574 A | * | 5/1988 | Hattori et al. | 428/409 |
| 4,842,729 A | * | 6/1989 | Buchan | 422/102 |
| 5,139,745 A | * | 8/1992 | Barr et al. | 356/244 |
| 5,353,112 A | * | 10/1994 | Smith | 356/244 |
| 5,537,202 A | * | 7/1996 | Komatsu et al. | 356/36 |
| 5,560,888 A | * | 10/1996 | Seto et al. | 422/104 |
| 5,633,724 A | * | 5/1997 | King et al. | 422/82.08 |
| 5,637,874 A | * | 6/1997 | Hozawa et al. | 422/52 |
| 5,741,463 A | * | 4/1998 | Sanadi | 422/102 |
| 5,772,967 A | * | 6/1998 | Wannlund et al. | 356/244 |
| 6,051,191 A | * | 4/2000 | Ireland | 356/246 |
| 6,047,614 A | * | 6/2000 | Hafeman et al. | 422/102 |
| 6,071,748 A | * | 6/2000 | Modlin et al. | 422/82.05 |
| 6,159,368 A | * | 12/2000 | Moring et al. | 422/104 |
| 6,159,425 A | * | 12/2000 | Edwards et al. | 422/63 |

DEVICES AND METHODS FOR SAMPLE ANALYSIS

CROSS-REFERENCES TO RELATED MATERIALS

This application is a continuation of PCT Patent application Ser. No. PCT/US99/16453, filed Jul. 21, 1999, which in turn claims priority from the following U.S. provisional patent applications: Ser. No. 60/093,768, filed Jul. 22, 1998; and Ser. No. 60/143,185, filed Jul. 9, 1999. These PCT and provisional applications are each incorporated herein by reference.

This application incorporates by reference the following U.S. patent applications: Ser. No. 09/156,318, filed Sep. 18, 1998; and Ser. No. 09/349,733, filed Jul. 8, 1999.

This application also incorporates by reference the following PCT patent applications: Ser. No. PCT/US98/23095, filed Oct. 30, 1998; Ser. No. PCT/US99/01656, filed Jan. 25, 1999; Ser. No. PCT/US99/03678, filed Feb. 19, 1999; Ser. No. PCT/US99/08410, filed Apr. 16, 1999; and Ser. No. PCT/US99/16057, filed Jul. 15, 1999.

This application also incorporates by reference the following U.S. provisional patent applications: Ser. No. 60/094,275, filed Jul. 27, 1998; Ser. No.60/094,276, filed Jul. 27, 1998; Ser. No.60/094,306, filed Jul. 27, 1998; Ser. No. 60/100,817, filed Sep. 18, 1998; Ser. No. 60/100,951, filed Sep. 18, 1998; Ser. No. 60/104,964, filed Oct. 20, 1998; Ser. No. 60/114,209, filed Dec. 29 , 1998 ; Ser. No. 60/116,113, filed Jan. 15, 1999; Ser. No. 60/117,278, filed Jan. 26, 1999; Ser. No. 60/119,884, filed Feb. 12, 1999; Ser. No. 60/121,229, filed Feb. 23, 1999; Ser. No. 60/124,686, filed Mar. 16, 1999; Ser. No. 60/125,346, filed Mar. 19, 1999; Ser. No. 60/126,661, filed Mar. 29, 1999; Ser. No. 60/130,149, filed Apr. 20, 1999; Ser. No. 60/132,262, filed May 3, 1999; Ser. No. 60/132,263, filed May 3, 1999; Ser. No. 60/135,284, filed May 21, 1999; Ser. No. 60/136,566, filed May 28, 1999; Ser. No. 60/138,311, filed Jun. 9, 1999; Ser. No. 60/138,438, filed Jun. 10, 1999; Ser. No. 60/138,737, filed Jun. 11, 1999; Ser. No. 60/138,893, filed Jun. 11, 1999; and Ser. No. 60/142,721, filed Jul. 7, 1999.

This application also incorporates by reference the following publications: Max Born and Emil Wolf, *Principles of Optics* (6$^{th}$ ed. 1980); Richard P. Haugland, *Handbook of Fluorescent Probes and Research Chemicals* (6$^{th}$ ed. 1996); and Joseph R. Lakowicz, *Principles of Fluorescence Spectroscopy* (1983).

FIELD OF THE INVENTION

The invention relates to techniques for analyzing samples. More particularly, the invention relates to devices and methods for containing and optically analyzing small sample volumes.

BACKGROUND OF THE INVENTION

The proliferation of biological targets and candidate drug compounds in high-throughput screening and the increased interest in characterizing the human genome have created a significant need for rapid, efficient, and reproducible analysis of many samples. Moreover, there often is a significant need to perform assays in high-throughput screening, genomics, and other applications, with minimal sample volumes that conserve potentially precious or costly reagents without sacrificing sensitivity and reproducibility.

Microscopists in particular have developed procedures for handling small sample volumes. A common format for microscopically analyzing biological samples is to sandwich the sample between parallel surfaces, such as opposing surfaces on a glass slide and coverslip. Unfortunately, microscope slides have significant limitations, particularly for performing quantitative assays in a reproducible high-throughput testing mode. First, microscope slides are usually assembled manually, which typically is slow and subject to operator variability or error, such as bubble formation. Second, the thickness of a sample sandwiched between surfaces of a microscope slide and coverslip can vary with sample volume, because the sample tends to spread between the surfaces until it reaches the edges of the smaller of the surfaces. Variations in sample thickness can cause variations in results, depending on the assay. Third, microscope slides often leave samples at least partially exposed to the ambient environment, which can cause analyte concentrations to vary if evaporation occurs. Variations in analyte concentration can kill cells and perturb binding rates and coefficients.

SUMMARY OF THE INVENTION

The invention provides devices and methods for containing and analyzing small sample volumes that are sandwiched between solid surfaces. The devices may include an automated drive mechanism that controls the relative positions of the surfaces and an environmental-control mechanism that controls the humidity, temperature, and/or other environmental conditions around the small sample volume. In some embodiments, at least one of the surfaces has a light-transmissive window for allowing optical analysis of a sample contained between the surfaces.

DESCRIPTION OF THE INVENTION

Figure 1:
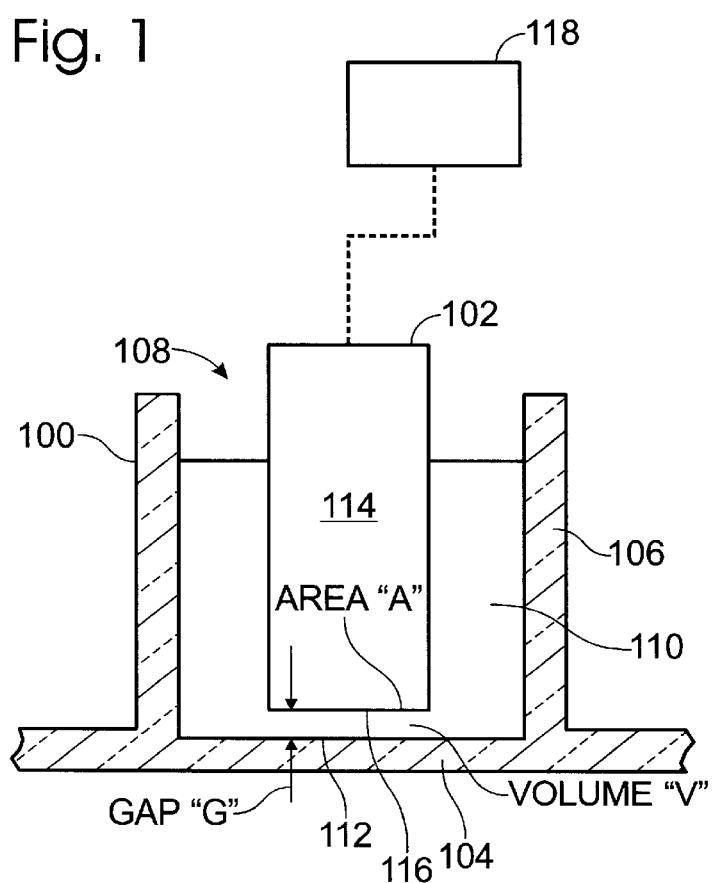
FIG. 1 is a partially schematic cross-sectional view of a sample-analysis device constructed in accordance with the invention, showing a luminescence modulator.

The invention provides devices and methods for containing and/or analyzing small sample volumes that are sandwiched between solid surfaces. The analysis may include luminescence, absorbance, scattering, and radiography, among others. A suitable optical device capable of analyzing samples from above and/or below a sample holder is described in U.S. patent application Ser. No. 09/160,533, which is incorporated herein by reference. The analysis also may include aspects of sample preparation, at least to the extent that such preparation is used to analyze sample constituents. The solid surfaces may be formed on the wall of a microplate, on a glass slide or cover slip, on a bulk solution displacement member, or on numerous other solid surfaces, including silica wafers and semiconductor substrates.

The invention may be used to form thin samples in relatively large-volume samples by excluding excess sample from an analysis area. Such an approach may be used when an assay protocol requires detection of chemical reactions or events occurring near a surface, such as a reaction involving a reagent that is bound to the surface. In this situation, it may be desirable to avoid optical emission or background from bulk solution remote from the surface. The invention provides a mechanical bulk displacement device for this purpose.

The invention also may be used to automatically process samples in a precisely controlled thin-layer format, including forming thin samples from relatively small-volume samples by spreading the sample across an analysis area. Such an approach may be used when it is desirable uniformly to spread, contain, and control a sample in a thin layer, for example, in a procedure such as nucleic acid hybridization to detect specific nucleic acids or immunostaining to detect specific proteins.

One aspect of the invention provides devices and methods for modulating (and usually reducing) luminescence from unbound luminophores in luminescence surface assays in relatively large-volume samples. Relatively large-volume samples are samples in which at least a portion of the sample resides outside the volume formed by the opposed surfaces provided by the invention. Luminescence is the emission of light from excited electronic states of atoms or molecules. Luminescence generally refers to all kinds of light emission, except incandescence, and may include photoluminescence and chemiluminescence, among others. In photoluminescence, including fluorescence and phosphorescence, the excited electronic state is created by the absorption of electromagnetic radiation. In chemiluminescence, which includes bioluminescence, the excited electronic state is created by a transfer of chemical energy.

Luminescence assays are assays that use luminescence emissions from luminescent analytes ("luminophores") to study the properties and environment of the analyte, as well as binding reactions and enzymatic activities involving the analyte, among others. In this sense, the analyte may act as a reporter to provide information about another material or target substance that may be the focus of the assay. Luminescence assays may involve various aspects of the luminescence, including its intensity, polarization, and lifetime, among others. Luminescence assays also may involve time-independent (steady-state) and/or time-dependent (time-resolved) properties of the luminescence.

Detecting surface binding using luminescence methods may require detecting changes in the relative numbers of bound and/or unbound luminophores. Unfortunately, if binding occurs adjacent bulk solution, there typically will be many fewer bound luminophores than unbound luminophores. Under such conditions, changes in the number of bound luminophores will be difficult to detect because the observed luminescence will be (vastly) dominated by luminescence from unbound luminophores. Similarly, changes in the number of unbound luminophores will be difficult to detect because the number of unbound luminophores will be relatively unaffected by binding.

The invention provides devices and methods for modulating (and usually reducing) luminescence from unbound luminophores in luminescence surface assays. Generally, the devices and methods function by displacing unbound luminophores from the vicinity of the surface, so that there are fewer unbound luminophores adjacent the surface to generate luminescence. This displacement may be performed using any suitable mechanism, including positioning a minimally luminescent, substantially impermeable material in close proximity to the surface.

FIG. 1 shows a sample holder 100 for holding a fluid sample for a luminescence surface assay, and a luminescence modulator 102 for modulating luminescence from unbound luminophores in the fluid sample during the surface assay.

Sample holder 100 generally comprises any mechanism for holding a fluid sample for a luminescence surface assay. In FIG. 1, sample holder 100 includes a substantially planar bottom wall 104 and at least one side wall 106 joined to the bottom wall to form a sample space 108 for holding a fluid sample 110. In addition, bottom wall 104 includes an assay surface 112 adjacent sample space 108 for performing a luminescence surface assay. Assay surface 112 may be at least partially transparent, so that at least a portion of light incident on assay surface 112 may be transmitted through the surface to detect binding at the surface. Assay surface 112 may be selected or treated to modify its optical properties, to facilitate cell growth, and/or to bind molecules of interest.

Luminescence modulator 102 generally comprises any mechanism for displacing fluid near a surface, so that the number of luminophores adjacent the surface may be modulated. In FIG. 1, luminescence modulator 102 includes an excluder 114 configured to displace fluid from near a surface.

Excluder 114 may take a variety of forms, so long as at least a portion of the excluder is dimensioned to fit within a sample holder. In FIG. 1, sample holder 100 and excluder 114 are substantially rectangular (or cylindrical), with the sample holder being slightly larger than the excluder. Excluder 114 may include a displacement surface 116 that complements assay surface 112 of the sample holder. In some applications, displacement surface 116 may be used as an additional assay surface, effectively doubling the number of bound luminophores.

Excluder 114 may be formed of a variety of materials, so long as such materials are only minimally luminescent, where minimally luminescent generally means less luminescent than the luminophores replaced by the excluder in a given assay. In some embodiments, the excluder may be opaque. In these embodiments, the excluder may include carbon black or other suitable materials to reduce autoluminescence. In other embodiments, the excluder may be reflective. In yet other embodiments, the excluder may be at least partially transparent, so that the sample may be analyzed through the excluder. In these embodiments, the excluder may have a higher index of refraction than the fluid. If the assay surface of the sample holder also is at least partially transparent, the sample may be analyzed through either or both the excluder and the sample holder, corresponding to top and bottom in FIG. 1.

Luminescence may be detected using an optical device having a detector in one or more of various positions relative to the assay surface, including above and/or below the assay surface.

The luminescence modulator may be used by positioning the excluder within a sample holder containing a sample and then exciting luminescence from bound luminophores adjacent the modulator. The excluder should be positioned within the depth of field of the light detection device used in the luminescence assay, so that the excluder displaces luminophores that otherwise would be detected during the assay. The sample holder ideally should be initially only partially filled, so that positioning of the excluder will not cause fluid to overflow. To simplify fluid displacement, the excluder may be smaller than the sample holder and/or include channels for fluid flow. The luminescence modulator also may be used by positioning the excluder within an empty sample holder and then adding sample.

The luminescence modulator provided by the invention allows a relatively large surface area to be sampled while excluding luminescence signal from the bulk volume. The modulator may be used with a large illumination area, such as that produced by a relatively low numerical aperture confocal system. The modulator also may be used by collecting a single measurement from each sample holder, because the data will be averaged over a large surface area and hence many luminophores. The need for scanning multiple areas or for performing multiple measurements that could be necessary with a relatively high numerical aperture confocal system should be reduced or eliminated, increasing speed and reducing data volume. These attributes are especially important in applications in which large numbers of samples must be analyzed, such as high-throughput screening.

The luminescence modulator also may obviate problems that would accompany the use of aspiration to remove bulk solution and decrease sample thickness. Aspiration is unsuitable for many assays because the thin layer of solution remaining after aspiration is subject to evaporation, which may kill cells and concentrate luminophores, perturbing binding. In addition, the thin layer may be of unknown or poorly characterized thickness, so that it may be difficult to determine the number of unbound luminophores remaining in the thin layer. Moreover, aspiration may require changing or washing aspiration equipment between assays to prevent cross-contamination.

The luminescence modulator also may include a driver 118 operatively connected to the excluder. The driver may be used automatically or robotically to position the excluder relative to a surface of the sample holder, and to hold or appropriately move the excluder during an assay. The driver also may be used for mixing a fluid sample by raising, lowering, and/or rotating the excluder within the sample. Such mixing may be used to accelerate reaction kinetics by augmenting diffusion.

Luminescence modulator 102 may be used to modulate the number of unbound luminophores and the relative numbers of bound and unbound luminophores adjacent assay surface 112. For example, assume that assay surface 112 and displacement surface 116 are substantially planar. The assay and displacement surfaces may then be used to define a volume V given by the product of the area A of the displacement surface and the separation or gap G between the assay and displacement surfaces 116. Assume also that the surface density of bound luminophores is $\rho_B$ (molecules/unit area) and that the volume density (concentration) of unbound luminophores is $C_U$ (molecules/unit volume). If a light detection device used in a luminescence surface assay detects from an area A' and depth of field D, the number of detectable bound luminophores within volume V will be $\rho_B A'$ and the number of detectable unbound luminophores within volume V will be $C_U A'G$, where G may range from 0 to D. The number of unbound luminophores and the relative numbers of bound and unbound luminophores within volume V may then be modulated by adjusting gap G. For example, to ensure that the number of bound molecules equals or exceeds the number of unbound luminophores within the detection volume (i.e., to ensure that $\rho_B A' \geq C_U A'G$), G must be less than or equal to $\rho_B/C_U$. In a typical cell assay, if there are about $10^3$ cells per square millimeter and about $10^5$ receptors binding a luminophore per cell, corresponding to a number density of about $10^8$ bound luminophores per square millimeter, and if the concentration of unbound luminophores is about 1 nanomolar, corresponding to a volume density of about $6 \cdot 10^8$ unbound luminophores per cubic millimeter, then G should be less than or equal to about 170 micrometers. Of course, this example is merely representative, and the luminescence modulator may be used with other luminophores, sample holders, and/or excluders, and according to other modulation criteria.

Luminescence surface assays suitable for use with the luminescence modulator include any luminescence technique capable of detecting luminescence originating at a surface. Such techniques may be based on fluorescence and/or phosphorescence, and may include fluorescence intensity, fluorescence polarization (FP), fluorescence resonance energy transfer (FRET), fluorescence lifetime (FLT), total internal reflection (TIR) fluorescence, fluorescence correlation spectroscopy (FCS), and fluorescence recovery after photobleaching (FRAP), and their phosphorescence analogs, among others. Multiple assays may be performed with the excluder in a constant position or with the excluder in various positions, for example, to keep the number of unbound luminophores detected substantially constant between samples.

Figure 2:
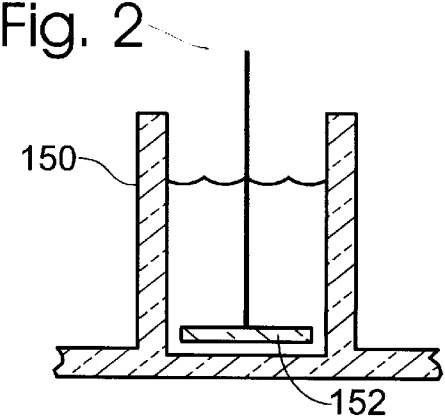
FIG. 2 is a partially schematic cross-sectional view of an alternative sample-analysis device constructed in accordance with the invention, showing a luminescence modulator having increased surface area and decreased fluid displacement.
Figure 3:
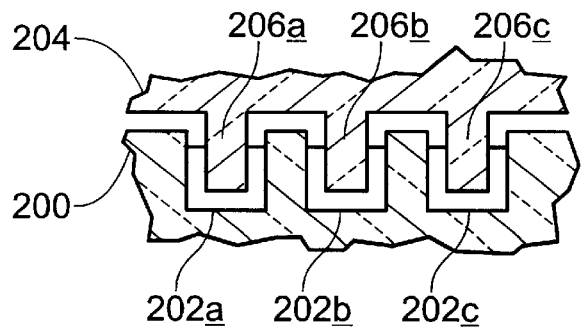
FIG. 3 is a partially schematic cross-sectional view of another alternative sample-analysis device constructed in accordance with the invention, showing a luminescence modulator for use with multi-well sample holders.

FIGS. 2–3 show alternative embodiments of the invention.

FIG. 2 shows a sample holder 150 and an excluder 152 configured to enhance area while reducing displaced volume. In cell applications, reduced displaced volume may reduce evaporation and enhance cell growth by ensuring that the cells receive sufficient metabolites.

FIG. 3 shows a sample holder 200 having a plurality of sample wells 202a,b,c, and an excluder 204 having a plurality of excluding members 206a,b,c configured to fit within the sample wells. Sample holders having a plurality of sample wells include microplates. In addition to sample holder 200, any of the sample-analysis devices and methods disclosed herein may be used with a plurality of sample wells.

Another aspect of the invention provides devices and methods to automatically process samples in a precisely controlled thin-layer format, including forming thin samples from relatively small-volume samples by spreading the sample across an analysis area. Here, relatively small-volume samples are samples having volumes comparable to the volume formed between the opposed surfaces provided by the invention.

The devices and methods may be used for preparing and/or containing samples for analysis. Sample preparation typically will involve incubating a surface-bound sample with a small quantity of soluble reagent. Surface-bound sample may include tissues, cells, and/or adsorbed or covalently bound species, such as nucleic acids, including DNA and RNA, proteins, lipid monolayers and bilayers, and beads, among others. Soluble reagent may include specific and nonspecific binding partners of the above, such as nucleic acid hybridization probes and antibodies, among others. Surface-binding assays may include competitive-type and sandwich-type polarization assays. Cell assays may include fluorescence in situ hybridization (FISH) for detecting and localizing specific nucleotide sequences, and immunoassays for detecting and localizing specific proteins. Here, FISH is a procedure in which fluorescently labeled polynucleotide probes are hybridized to sample DNA, typically to identify the genomic location of a gene or gene fragment. Tissue assays may include assays to stain or label particular cell types in a tissue containing a variety of cell types. Other assays may include micro-miniature applications, such as micro laboratories on a chip. Yet other assays and assay components such as labels may be found in Richard P. Haugland, *Handbook of Fluorescent Probes and Research Chemicals* (6$^{th}$ Ed. 1996), which is incorporated herein by reference.

Sample containment typically will involve holding a sample prepared as described above, but also may simply involve holding small-volume samples. Mechanisms for sample containment may include environmental control mechanisms for reducing contamination and evaporation. Small thin samples are especially susceptible to contamination and evaporation due to their relatively large surface-to-volume ratios. This susceptibility is compounded in hybridization and other labeling assays, in which small thin samples must be maintained for long times while hybridization occurs. Contamination can have various effects, depending on the contaminant. Evaporation also can have various effects, including killing cells and concentrating luminophores and other solutes, potentially perturbing binding. Further information regarding evaporation is presented in the Appendix.

Figure 4:
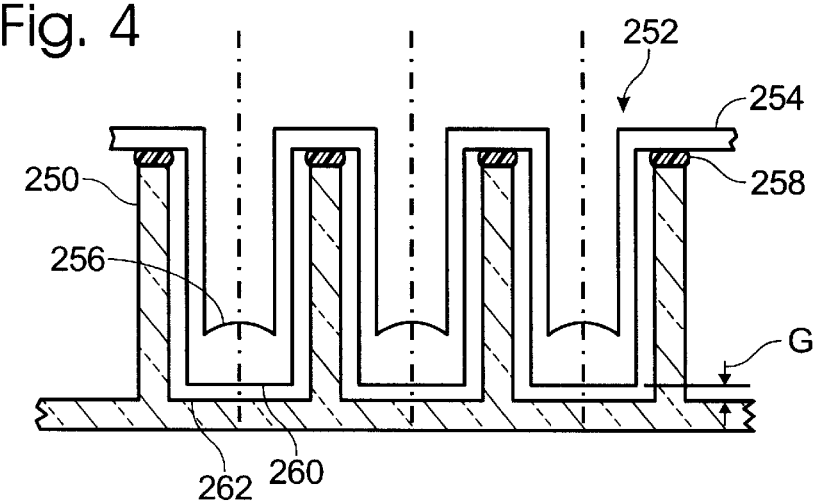
FIG. 4 is a partially schematic cross-sectional view of yet another alternative luminescence modulator constructed in accordance with the invention, showing a luminescence modulator having a lens for focusing light onto an assay surface.
Figure 5:
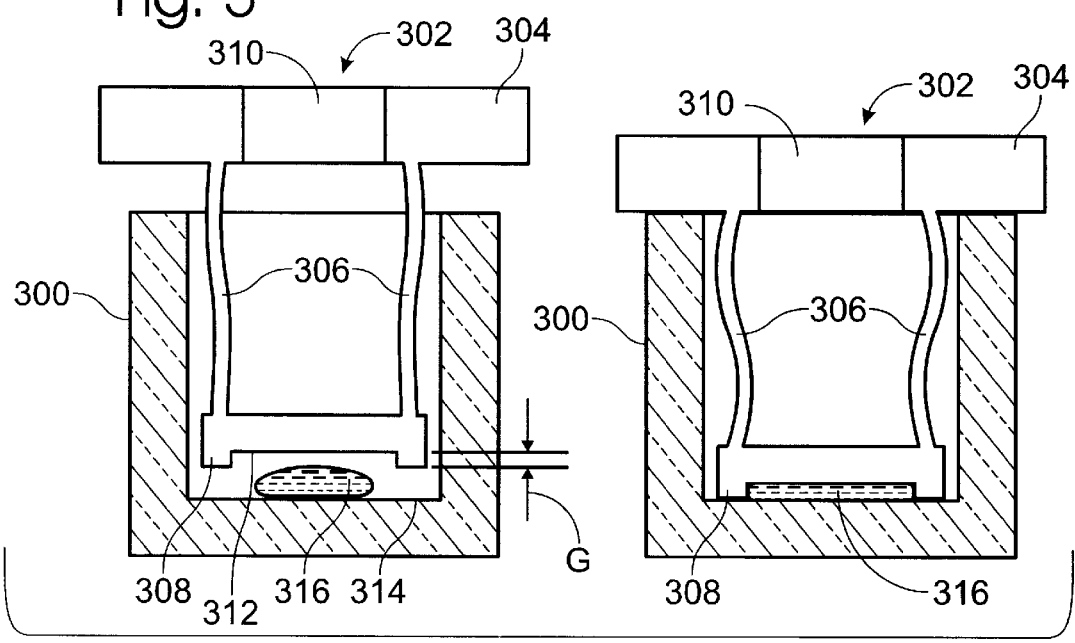
FIGS. 5 and 6 are partially schematic cross-sectional views of yet other alternative sample-analysis devices constructed in accordance with the invention, showing luminescence modulators having springs for biasing the modulators toward an assay surface.
Figure 6:
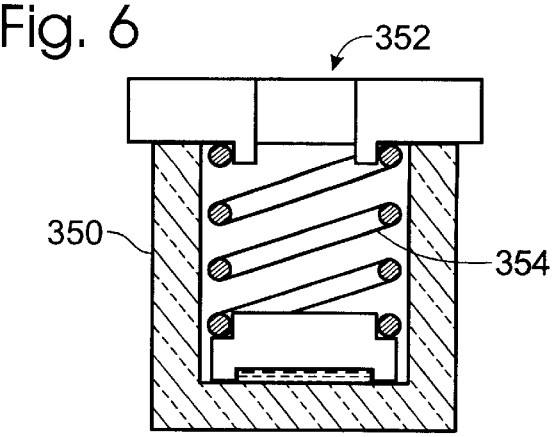

FIGS. 4–6 show other alternative embodiments of the invention. These embodiments are especially suitable for use with microplates.

FIG. 4 shows a sample holder 250 and an excluder 252 having a cover 254 and a lens 256. Cover 254 may be used to cover the sample holder and includes a sealing fixture or gasket 258 so that the cover may be sealed to the sample holder for environmental control to reduce contamination and evaporation. The sample holder and excluder may be sized to leave a controlled gap G between a displacement surface 260 of the excluder and an opposed surface 262 of the sample holder. Lens 254 may be used to focus light through the excluder and onto a sample 264 contained within the gap.

FIG. 5 shows two views of a sample holder 300 and an excluder 302 having a cover 304, a biasing element 306, a stop element 308, and an aperture or window 310. Cover 304 may be used to cover the sample holder. Biasing element 306 may be used to bias a displacement surface 312 of the excluder toward an opposed surface 314 of the sample holder. The biasing element at least partially compensates for variations in the sample holder, including out-of-flatness and discrepancies in dimensions, well depths, and other process variables; such variations are common in injection molded sample holders, such as microplates. The biasing element may include a soft molded spring or other structure capable of providing a suitable biasing force. Here, spring generally refers to a device that returns to its original shape after being forced out of shape. The biasing element also may include a fluid path. Stop element 308 may be used to set a minimum distance or gap G between the displacement surface and opposed surface. Aperture or window 310 may be used to provide optical access to a sample 316 contained within the gap.

FIG. 6 shows a sample holder 352 and an excluder 352 having an alternative biasing element 354 and other features. Alternative biasing element 354 may include a spiral spring.

These embodiments may be constructed for low-cost, disposable use with automated systems and high-throughput screening. For example, the spring in FIGS. 5 and 6 may be used as a passive actuator to create a sample gap or analysis chamber, without requiring an automated drive mechanism or other actuation means. Moreover, the lens in FIG. 4 may be used in lieu of or in addition to other optics associated with an optical device.

FIGS. 7–12 show yet other embodiments of the invention. These embodiments are especially suitable for use as automated slide-processing chambers. These embodiments are sized to match the slides and sample volumes with which they are used, and may be relatively compact if sized for standard microscope slides and associated sample volumes.

Figure 7:
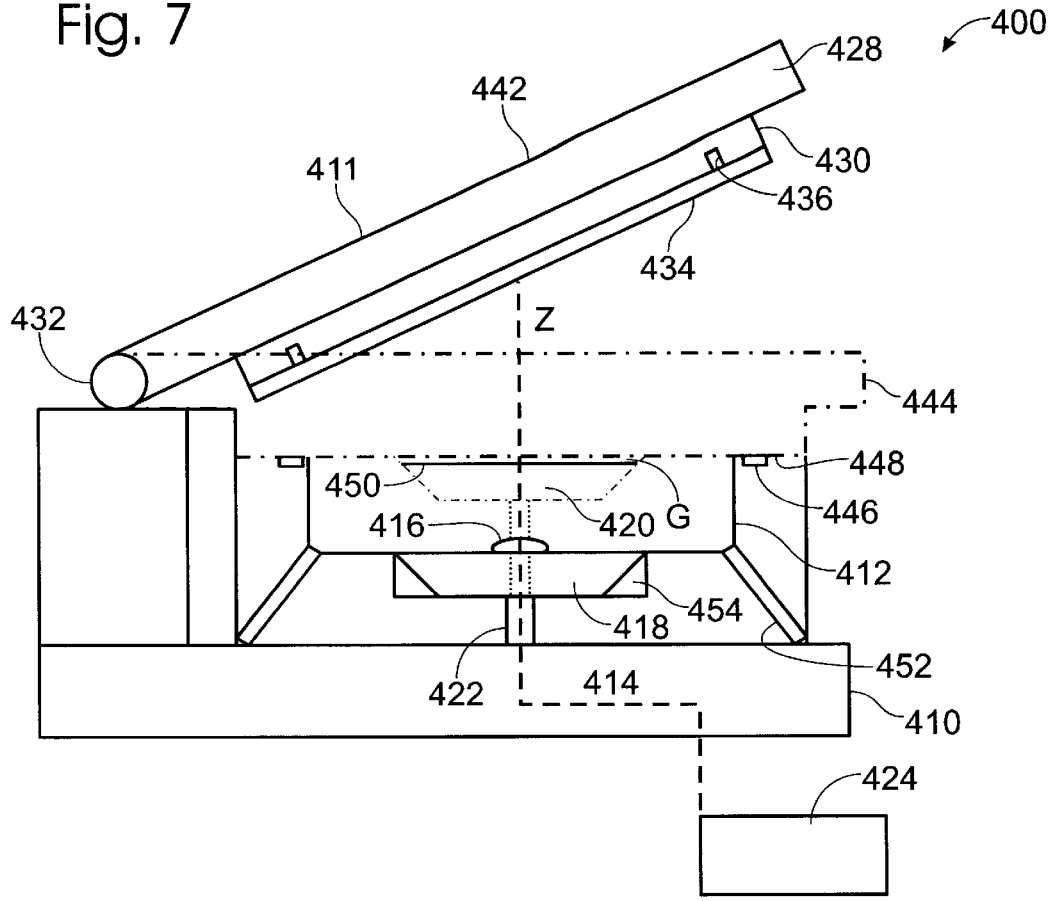
FIG. 7 is a cross-sectional side view of yet another sample-analysis device constructed in accordance with the invention, showing an automated slide-processing chamber.
Figure 8:
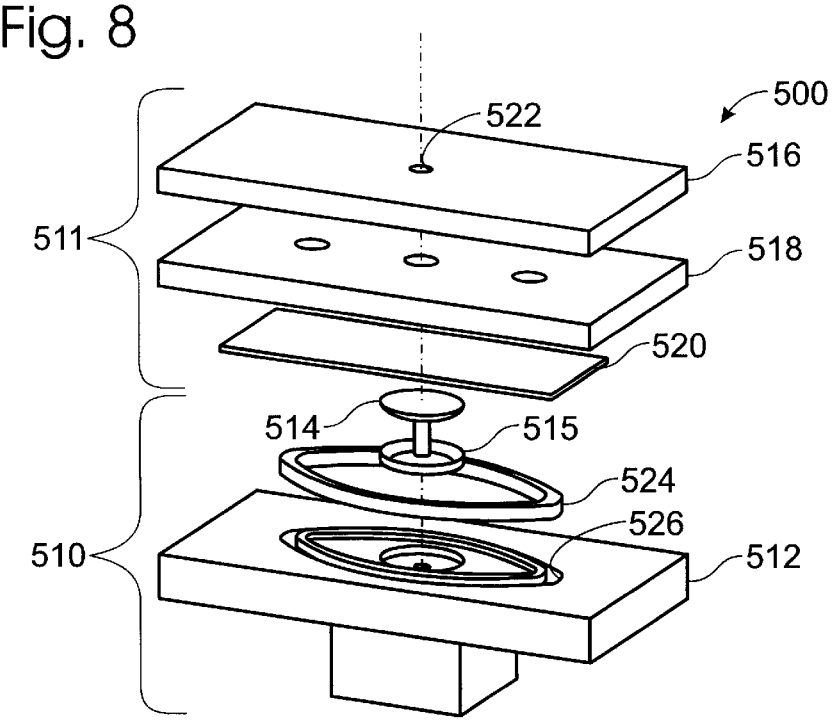
FIG. 8 is an exploded perspective view of a yet another sample-analysis device constructed in accordance with the invention, showing an alternative automated slide-processing chamber.
Figure 9:
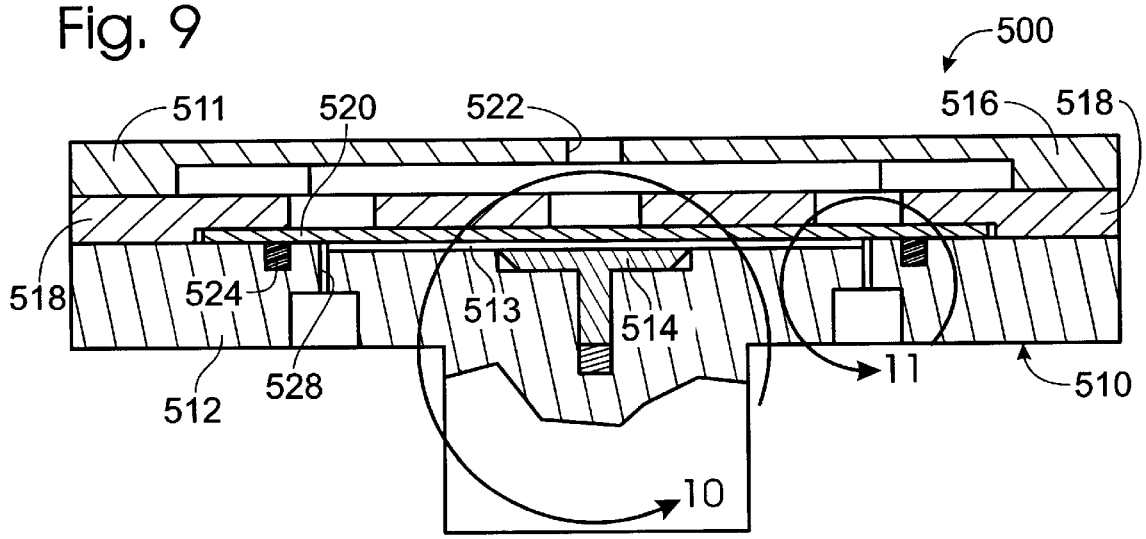
FIG. 9 is a cross-sectional side view of the sample-analysis device of FIG. 8.
Figure 10:
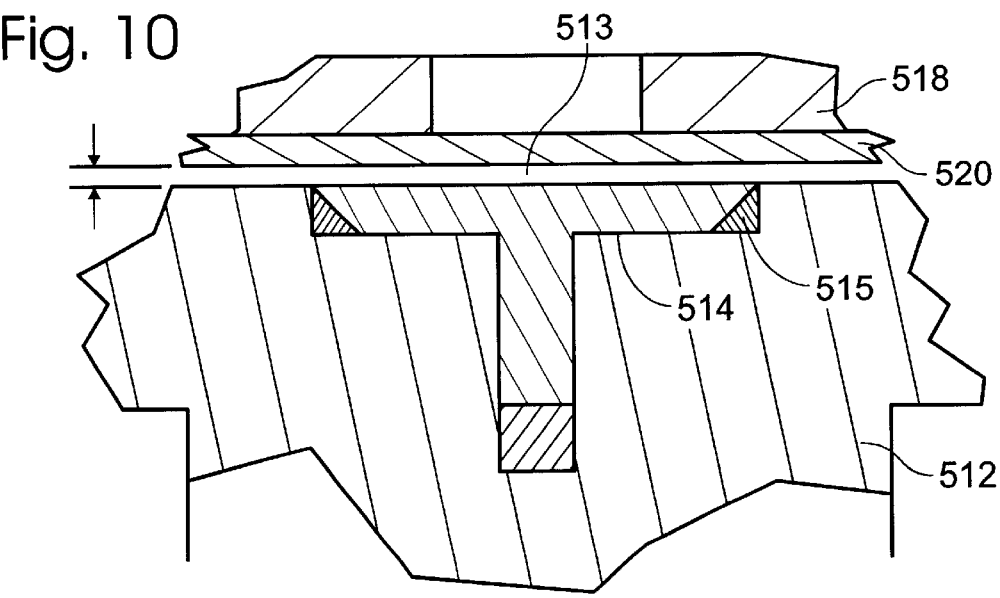
FIG. 10 is a partial cross-sectional side view of the sample-analysis device of FIG. 9.
Figure 11:
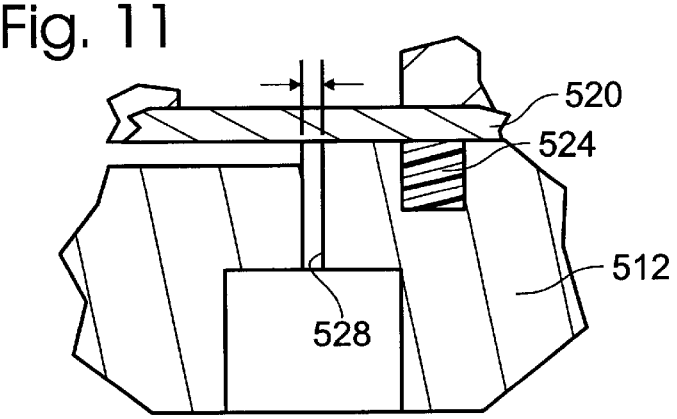
FIG. 11 is another partial cross-sectional side view of the sample-analysis device shown in FIG. 9.

FIG. 7 shows a sample container 400 having a base 410 and an opposable top plate member 411 configured to abut a portion of the base. Base 410 includes an analysis chamber 412 (formed atop the base) and a moveable sample platform 414 for supporting a sample 416 within the analysis chamber. Sample 416 may include a small (e.g., 1–20 microliter) volume of fluid, positioned directly on the sample platform or on a suitable substrate such as a coverslip positioned on the sample platform. Sample platform 414 is shown in solid lines in a lowered loading position 418 substantially coplanar with the bottom of the analysis chamber. Sample platform 414 is shown in dashed lines in a raised analyzing position 420 where it presents the sample for analysis. Such analysis may include processing the sample together with an opposed slide in preparation for an assay, such as a labeling assay. Sample platform 414 may be moved automatically or robotically between the loading and analyzing positions by a piston 422 and an associated drive mechanism 424.

Top plate member 411 includes a support member 428, a slide carrier 430, and a hinge 432. Slide carrier 430 is used to carry a slide 434, which may be secured to the slide carrier using a vacuum provided via a vacuum groove 436, among other mechanisms. Slide 434 may include any suitable substrate, such as a microscope slide, coverslip, or (DNA) microchip, among others. Hinge 432 is used pivotably to connect top plate member 411 to base 410, so that the top plate member may be used as a door to open and close access to analysis chamber 412. Top plate member 411 is shown in solid lines in an open loading position 442 in which slide carrier 434 is presented for mounting and dismounting a slide. Top plate member 411 is shown in dashed lines in a closed analyzing position 444 where slide 434 is presented for analysis adjacent analysis chamber 412. Top plate member 411 may be moved manually or automatically between the open and closed positions. Such movement may be along an axis Z, where the slide and sample support include surfaces substantially perpendicular to the axis.

Top plate member 411 may be used in the closed position to seal analysis chamber 412 from the external environment. In this position, the top plate member covers the analysis chamber, and a seal 446 creates a seal between slide 434 and an upper edge 448 around the analysis chamber. The interior of closed analysis chamber 412 then can be environmentally controlled to reduce sample contamination and evaporation, maintain a desired temperature, and/or generally preserve constituents of the sample.

Sample container 400 may be used as follows, where the order of the steps may be varied as desired and appropriate. First, top plate member 411 is moved into open loading position 442, and sample platform 414 is moved into lowered loading position 418. Second, slide 434 is mounted to slide carrier 434, and sample 416 is added to sample platform 414, for example, by using a syringe. Third, top plate member 411 is moved into closed analyzing position 444, and sample platform 414 is moved into raised analyzing position 420. This automatically brings sample platform 414 into closely spaced proximity with a surface 448 of slide 434, leaving a small precise gap G for presenting sample 416 in a thin precisely controlled layer. This gap may be controlled by the driver or by a spacer positioned, for example, adjacent the slide, sample platform, and/or piston. If sample 416 includes a small volume of fluid, sample 416 may spread out against surface 450 by capillary action, such that the thickness of the sample is determined by G, and the area of the sample is determined by the area of sample platform 414 (or by the volume of the sample if the quotient of the volume and G is less than the area of the sample platform). Fourth, sample platform 414 may be lowered, and sample 416 may be removed by washing and new sample may be added using inlet/outlet channels 452 to analysis chamber 412. A wedge seal 454 adjacent sample platform 414 reduces the likelihood that wash fluid will leak by the sample platform during washing. Fifth, following processing, slide 434 may be viewed in analysis chamber 412, if for example top plate member includes a viewing aperture or window; alternatively, top plate member 411 may be moved back into open loading position 442, sample platform 414 may be moved back into lowered loading position 418, and slide 434 may be removed for viewing elsewhere. Sixth, if desired, all or parts of this process may be repeated, for example, to incubate a second sample against a given slide, or to prepare a second slide.

Sample container 400 may be used reproducibly to create thin samples having a preselected thickness. The analyzing chamber may be used to reduce contamination and evaporation, reducing or eliminating the need to place sealing material around the slide or fluid area, and leaving the sample area accessible for washing or receiving new reagents. The samples may be used in various assays, making the assays more reproducible and efficient.

Sample container 400 also may be used to overcome difficulties associated with manual sample preparation. The container may be used to reduce the number and size of bubbles formed within a thin sample, because the volume of sample, the geometry of the sample platform and slide, and the rate at which the sample platform is made to approach the slide may be adjusted until fewer and/or smaller bubbles are produced, and then the same conditions may be used for subsequent samples. The container also may be used to reduce the time required to form thin samples. The container also may be used to reduce the person-to-person and sample-to-sample variations that arise with manual sample preparation.

FIGS. 8–11 show another sample container 500 having a base 510 and opposable top plate member 511. Sample container 500 shares many similarities with sample container 400 in FIG. 7; however, in sample container 500, base 510 and top plate member 511 are set rather than hinged together.

Base 510 includes a bottom plate 512, an analysis chamber 513, a sample platform 514 for supporting a sample, and a wedge seal 515 for reducing leakage. Sample platform 514 is moveable between loading and analyzing positions, as described above with reference to sample container 400.

Top plate member 511 includes a support member 516 and a slide carrier 518 for carrying a slide 520. Slides may be secured to slide carrier 518 using a vacuum provided via a vacuum groove 522. Top plate member 511 may be sealed to base 510 using a sealing gasket 524 that contacts slide 520 from a groove 526 in base 510.

Sample container 500 may be used for sample preparation and/or analysis, as described above with reference to sample container 400. Sample platform 514 and slide 520 may be brought in and out of contact automatically, within a sealed chamber. The sample and sample chamber may be washed or flushed using inlet/outlet channels 526 and may be heated using a heater positioned, for example, adjacent bottom plate 512.

Figure 12:
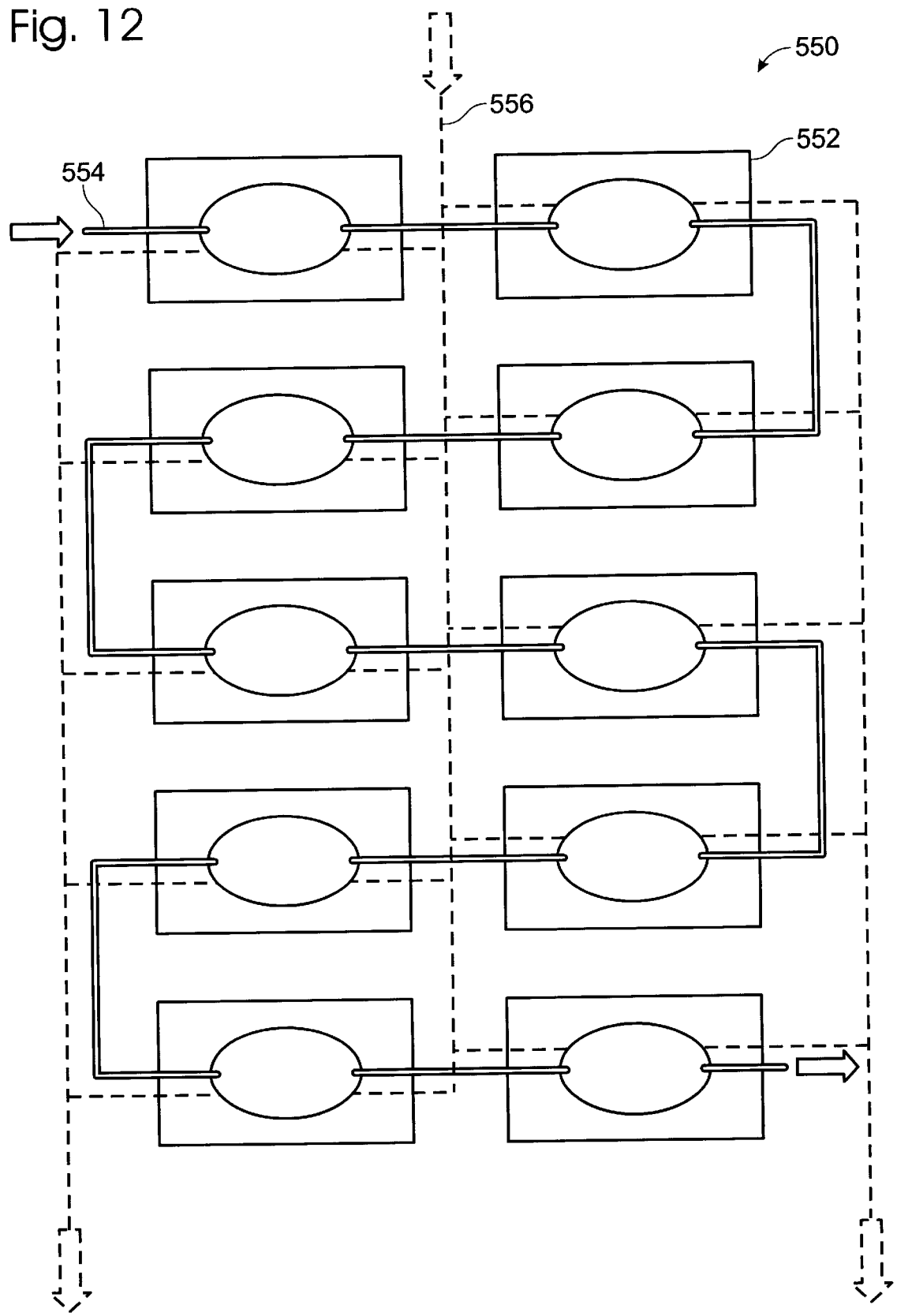
FIG. 12 is a schematic view of a multi-sample container system constructed in accordance with the invention.

FIG. 12 shows an array 550 of sample holders 552, such as automated slide-processing chambers, with two alternative wash or flushing networks. In one embodiment, a conduit system 554 (shown in solid lines) provides wash or flush channels to plural containers in series from a common source to a waste receiver. In another embodiment, another conduit system 556 (shown in dashed lines) provides wash or flush channels to plural containers in parallel from a common source. Efflux from this conduit system may be routed to a plurality of waste receivers or may be recombined and routed to a single waste receiver. In yet other embodiments, conduit systems may provide wash or flush channels in combinations of series and parallel, such as in series through rows of containers and in parallel to the rows of containers.

EXAMPLES

Selected aspects of the invention also may be described as recited in the following numbered paragraphs:

1. A device for containing a fluid sample to be analyzed, the device comprising a first surface, a second surface, and an automated drive mechanism that moves the second surface into closely spaced proximity with the first surface for containing the sample, such that the sample is in simultaneous contact with the first and second surfaces.

2. The device of paragraph 1, wherein at least one of the surfaces has a light-transmissive window through which optical analysis can be performed.

3. The device of paragraph 1 further comprising an environmental control mechanism for controlling the environment around a sample sandwiched between the surfaces.

4. The device of paragraph 3, wherein the environmental control mechanism includes a sealed chamber that contains the surfaces.

5. The device of paragraph 1 further comprising a sealing fixture between the surfaces so that a sample contained between the surfaces is sealed off from an ambient environment.

6. The device of paragraph 1 further comprising a spacing mechanism defining a thin gap between the surfaces for containing a sample to be optically analyzed.

7. The device of paragraph 1, wherein the automated drive mechanism includes a piston.

8. The device of paragraph 1, wherein each of the surfaces is substantially parallel to the other surface and perpendicular to a Z-axis, at least one of the surfaces being moveable along the Z-axis.

9. The device of paragraph 1, wherein the first surface is on a door member that is pivotally hinged relative to the second surface.

10. The device of paragraph 1, wherein the first surface is located in a bottom of a microplate well.

11. The device of paragraph 1 further comprising reagents selected from the group consisting of polypeptides, polynucleotides, luminescently labeled polypeptides, luminescently labeled polynucleotides, and luminophores, bound to at least one of the surfaces.

12. The device of paragraph 1, wherein the gap has an adjustable height.

13. The device of paragraph 1, wherein at least one of the surfaces is rotatable relative to the other surface to mix a sample contained between the surfaces.

14. The device of paragraph 1 further comprising an automated flushing mechanism that clears the sample from between the surfaces.

15. The device of paragraph 1, wherein the surfaces are substantially planar.

16. The device of paragraph 1, wherein at least one of the surfaces is curved.

17. A device for containing a fluid sample to be analyzed, the device comprising a first platen, a second platen, and a drive mechanism that moves the second platen toward the first platen into closely spaced proximity with the second platen for containing the sample, such that the sample is in simultaneous contact with the first and second surfaces, wherein each platen is located at different points along a Z-axis, perpendicular to the Z-axis.

18. The device of paragraph 17, wherein at least one of the platens has a light-transmissive window through which optical analysis can be performed.

19. The device of paragraph 17 further comprising reagents selected from the group consisting of polypeptides, polynucleotides, luminescently labeled polypeptides, luminescently labeled polynucleotides, and luminophores, bound to at least one of the surfaces.

20. The device of paragraph 17 further comprising an environmental control mechanism for controlling the environment around a sample sandwiched between the platens.

21. The device of paragraph 20, wherein the environmental control mechanism includes a sealed chamber that contains the surfaces.

22. The device of paragraph 17, wherein the drive mechanism includes a piston that spring biases the first platen toward the second platen.

23. A method of analyzing a sample, the method comprising depositing a sample on a first surface, spreading the sample across the first surface by robotically moving a second surface into contact with the sample, and defining a thin gap between the surfaces that is independent of the volume of the sample.

24. The method of paragraph 23 further comprising the step of sealing the sample within an environmentally controlled chamber.

25. The method of paragraph 23 further comprising the step of providing a light-transmissive window in at least one of the surfaces.

26. The method of paragraph 25 further comprising the step of performing an optical analysis through the window on the sample contained between the surfaces.

27. The method of paragraph 23 further comprising depositing a second sample on a third surface, spreading the second sample across the third surface by robotically moving a fourth surface into contact with the second sample, and defining a second thin gap between the third and fourth surfaces that is independent from the volume of the second sample.

28. The method of paragraph 27 further comprising the step of providing a common flush network to the gaps.

29. The method of paragraph 28 further comprising the step of serially linking the flush network through the gaps.

30. The method of paragraph 28 further comprising the step of linking in parallel the flush network through the gaps.

31. A sample container for optical examination, the sample container comprising a slide surface, a cover surface in closely spaced coplanar proximity to the slide surface, and an environmental control mechanism that controls the environment around the sample sandwiched between the surfaces.

32. An examination platform comprising a sample holder having one or more examination sites, a cover structure, each examination site having an oppositely corresponding sample-contacting surface on the cover structure, and a drive mechanism that automatically brings each sample-contacting surface and corresponding examination site into closely spaced proximity for performing optical analysis on samples contained at said one or more examination sites.

33. An examination chamber for labeling a substrate, the examination chamber comprising an environmentally controlled chamber having a bottom surface and a top opening, a removable cover configured to seal shut the top opening of the chamber, and a drive mechanism that robotically moves at least a portion of the bottom surface into closely spaced proximity to the cover, wherein at least one of the bottom surface and removable cover is configured to receive the substrate.

34. The examination chamber of paragraph 33, wherein at least one of the bottom surface and the cover has a light-transmissive window so that a sample sandwiched between the surface and the cover can be analyzed.

Appendix

The invention may include an environmental control mechanism for controlling humidity, temperature, and/or other environmental parameters adjacent the sample. This appendix describes issues relating to control of evaporation and hydration, in particular, the volume of fluid necessary for an environmental control mechanism to humidify an analysis chamber having a defined volume.

The following table shows the volume $V_v$ of saturated water vapor derived from a volume $V_f$ of fluid water as a function of temperature.

| T (C) | T (K) | P (mm Hg) | $V_v/V_f$ |
|---|---|---|---|
| 5 | 278.16 | 6.54 | 147,000 |
| 10 | 283.16 | 9.21 | 107,000 |
| 15 | 288.16 | 12.79 | 78,100 |
| 20 | 293.16 | 17.54 | 57,800 |
| 25 | 298.16 | 23.76 | 43,500 |
| 30 | 303.16 | 31.82 | 33,000 |
| 35 | 308.16 | 42.18 | 25,300 |
| 40 | 313.16 | 55.32 | 19,600 |

-continued

| T (C) | T (K) | P (mm Hg) | $V_v/V_f$ |
|---|---|---|---|
| 45 | 318.16 | 71.88 | 15,300 |
| 50 | 323.16 | 92.51 | 12,100 |
| 55 | 328.16 | 118.04 | 9,610 |
| 60 | 333.16 | 149.38 | 7,750 |
| 65 | 338.16 | 187.54 | 6,250 |
| 70 | 343.16 | 233.70 | 5,100 |

The ratio $V_v/V_f$ was derived from the following equation, where $R=6.24 \cdot 10^4$ cm$^3$(mm Hg)/K/mole is the gas constant, T is the absolute temperature in Kelvin, P is the pressure in millimeters of mercury (mm Hg), and $V_{molar}=18$ cm$^3$/mole is the molar volume of fluid water:

$$V_v/V_f = RT/PV_{molar} \tag{A1}$$

Equation A1 assumes that the water vapor behaves like an ideal gas, an assumption that should be good to within at least 10–20%. Sources of nonidealities include interactions between water molecules, surface tension, and solute effects. Effects of many nonidealities can be corrected using the International Steam Tables. Effects of surface tension decrease with fluid volume and are likely to be small for microliter samples, which have radii of curvature of about 1 millimeter. Effects of solutes can be corrected using formulae describing colligative properties and are likely to be small (about 1 percent) for physiological salt concentrations.

Generally, the volume of fluid water necessary to saturate a given volume of air can be determined by dividing the volume of air space to be humidified by the ratio $V_v/V_f$. However, if the air initially includes some moisture, so that its initial relative humidity is N %, the volume of fluid necessary to saturate the air will be reduced by N %.

Water will evaporate from both the sample and any hydration reservoir to achieve saturation. The relative contributions from each likely are proportional to their relative surface areas. Evaporation from the sample may be reduced by presaturating the analysis chamber.

Once saturation is achieved, water may move from a distilled-water reservoir to a buffered sample, due to the effects of solutes on vapor pressure, so that the volume of the sample will grow at the expense of the volume of the reservoir. However, this process is likely to be too slow to be important during most experiments, and can be reduced or eliminating by matching reservoir osmolarity to sample osmolarity.

Although the invention has been disclosed in its preferred forms, the specific embodiments thereof as disclosed and illustrated herein are not to be considered in a limiting sense, because numerous variations are possible. For example, the luminescence modulator may be used with any of the light detection devices, light detection methods, and sample holders described in the above-identified patent applications. Applicants regard the subject matter of their invention to include all novel and nonobvious combinations and subcombinations of the various elements, features, functions, and/or properties disclosed herein. No single feature, function, element or property of the disclosed embodiments is essential. The following claims define certain combinations and subcombinations of features, functions, elements, and/or properties that are regarded as novel and nonobvious. Other combinations and subcombinations may be claimed through amendment of the present claims or presentation of new claims in this or a related application. Such claims, whether they are broader, narrower, equal, or different in scope to the original claims, also are regarded as included within the subject matter of applicants' invention.

We claim:

1. A method for modulating the number of unbound luminophores adjacent a surface during a luminescence surface assay, the method comprising:
providing a sample holder for holding a sample, the sample holder including at least one assay surface configured for performing a luminescence surface assay;
at least partially filling the sample holder with a fluid sample having a population of luminophores, the luminophores capable of binding to the assay surface or to a substrate adjacent the assay surface, so that the sample includes bound and unbound luminophores;
detecting luminescence from the sample, the detected luminescence including at least a portion from bound luminophores and at least a portion from unbound luminophores; and
positioning an excluder near the assay surface, so that the portion of the detected luminescence arising from the unbound luminophores may be modulated.

2. The method of claim 1, wherein the sample holder is a microplate well.

3. The method of claim 2, wherein the assay surface is a bottom wall of the microplate well.

4. The method of claim 3, wherein the assay surface is at least partially transparent.

5. The method of claim 4, wherein the step of detecting luminescence includes reading through the assay surface from below the bottom wall.

6. The method of claim 5, wherein the excluder includes carbon black to reduce autoluminescence.

7. The method of claim 1, the excluder being at least partially transparent, wherein the step of detecting luminescence includes reading through the excluder from above the bottom wall.

8. The method of claim 7, wherein the bottom wall includes carbon black to reduce autoluminescence.

9. The method of claim 1, wherein the substrate adjacent the assay surface includes cells.

10. The method of claim 1, wherein the step of detecting luminescence from the sample includes measuring the luminescence using a light detection device.

11. The method of claim 10, wherein the step of positioning an excluder includes placing the excluder within the depth of field of the light detection device.

12. The method of claim 11, the excluder having a displacement surface, wherein the excluder includes a stop element configured to set the minimum distance between the displacement surface and assay surface.

13. The method of claim 1 further comprising mixing the sample by raising, lowering, or rotating the excluder.

14. The method of claim 1, the excluder including a displacement surface, wherein the assay surface and displacement surface are separated by at least about 10 micrometers.

15. The method of claim 1, the excluder including a displacement surface, wherein the assay surface and displacement surface are separated by no more than about 1 millimeter.

16. The method of claim 1, the excluder having a displacement surface, wherein the excluder includes a stop element configured to set the minimum distance between the displacement surface and the assay surface.

17. The method of claim 1, the excluder having a displacement surface, wherein the displacement surface is substantially planar.

18. The method of claim 1, the excluder having a displacement surface, wherein the displacement surface is concave.

* * * * *

UNITED STATES PATENT AND TRADEMARK OFFICE
CERTIFICATE OF CORRECTION

PATENT NO.    : 6,486,947 B2
DATED         : November 26, 2002
INVENTOR(S)   : Douglas N. Modlin, Amer El-Hage and John C. Owicki It is certified that error appears in the above-identified patent and that said Letters Patent is hereby corrected as shown below:

<u>Title page,</u>
Please delete Item [60] and replace it with the following:

-- Provisional application No. 60/093,768, filed on Jul. 22, 1998 and provisional application No. 60/143,185, filed on Jul. 9, 1999. --

Signed and Sealed this

Third Day of June, 2003

JAMES E. ROGAN
*Director of the United States Patent and Trademark Office*